(12) United States Patent
Larsen et al.

(10) Patent No.: US 10,828,427 B2
(45) Date of Patent: Nov. 10, 2020

(54) SHIELDED NEEDLE CANNULA

(71) Applicant: Novo Nordisk A/S, Bagsvaerd (DK)

(72) Inventors: Bjoern Gullak Larsen, Birkeroed (DK); Christoffer Busk Stormoen, Hvidovre (DK); Kurt Solgaard, Graested (DK); Thomas Olund Christensen, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 143 days.

(21) Appl. No.: 15/773,399

(22) PCT Filed: Nov. 11, 2016

(86) PCT No.: PCT/EP2016/077434
§ 371 (c)(1),
(2) Date: May 3, 2018

(87) PCT Pub. No.: WO2017/084976
PCT Pub. Date: May 26, 2017

(65) Prior Publication Data
US 2018/0318522 A1   Nov. 8, 2018

(30) Foreign Application Priority Data
Nov. 19, 2015  (EP) .................................. 15195375

(51) Int. Cl.
*A61M 5/32* (2006.01)
*A61M 5/50* (2006.01)
(Continued)

(52) U.S. Cl.
CPC .......... *A61M 5/3245* (2013.01); *A61M 5/001* (2013.01); *A61M 5/24* (2013.01); *A61M 5/326* (2013.01); *A61M 5/50* (2013.01); *A61M 2005/3247* (2013.01); *A61M 2005/3267* (2013.01)

(58) Field of Classification Search
CPC .............. A61M 5/3245; A61M 5/3243; A61M 2005/3247; A61M 5/326; A61M 25/0618; A61M 25/0625; A61M 25/0631; A61M 2005/2013; A61M 5/50
See application file for complete search history.

(56) References Cited

U.S. PATENT DOCUMENTS

| 6,406,459 B1 * | 6/2002 | Allmon ............... A61M 5/3273 |
|---|---|---|
| | | 604/192 |
| 2003/0014018 A1 | 1/2003 | Giambattista et al. |

(Continued)

FOREIGN PATENT DOCUMENTS

| CN | 101563124 A | 10/2009 |
|---|---|---|
| WO | 01/91837 A1 | 12/2001 |
| WO | 2014195183 A1 | 12/2014 |

*Primary Examiner* — Nathan R Price
*Assistant Examiner* — Melissa A Snyder
(74) *Attorney, Agent, or Firm* — Wesley Nicolas

(57) ABSTRACT

The invention relates to an injection system or a needle assembly in which a needle cannula secured to an injection device is shielded by a axially movable needle shield. Should the needle cannula be exposed to a force above a predetermined value e.g. if a user drops the injection device onto a hard surface, a locking mechanism will automatically lock and block further movement of the axially movable needle shield and thus render the injection device unusable.

12 Claims, 3 Drawing Sheets

(51) Int. Cl.
 *A61M 5/00* (2006.01)
 *A61M 5/24* (2006.01)

(56) References Cited

U.S. PATENT DOCUMENTS

| | | | |
|---|---|---|---|
| 2003/0060776 A1 | 3/2003 | Heiniger | |
| 2006/0264830 A1* | 11/2006 | Hommann | A61M 5/2033 604/136 |
| 2006/0270984 A1* | 11/2006 | Hommann | A61M 5/2033 604/134 |
| 2007/0265568 A1* | 11/2007 | Tsals | A61M 5/2033 604/136 |
| 2009/0299295 A1 | 12/2009 | Rubinstein et al. | |
| 2011/0178501 A1* | 7/2011 | Cleathero | A61M 5/2033 604/506 |
| 2012/0179110 A1 | 7/2012 | Gratwohl et al. | |
| 2014/0236095 A1 | 8/2014 | Slemmen et al. | |
| 2015/0039009 A1* | 2/2015 | Tamano | A61B 17/3417 606/186 |

* cited by examiner

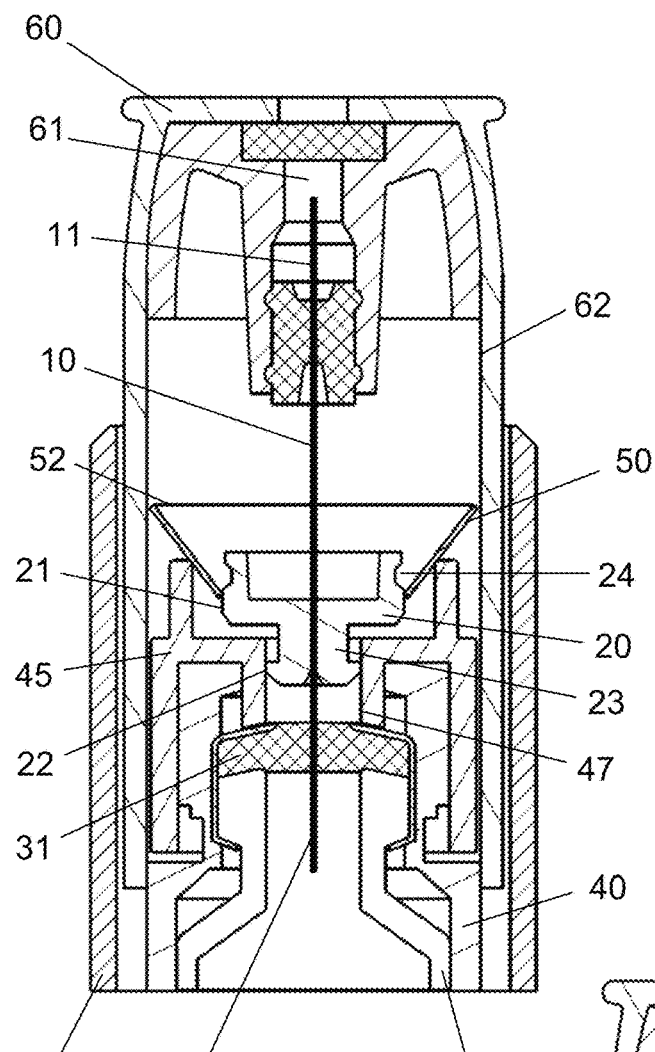
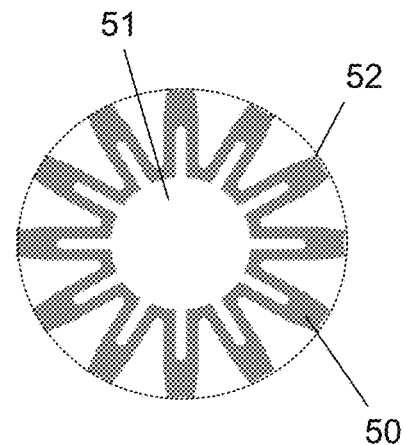
Fig. 2
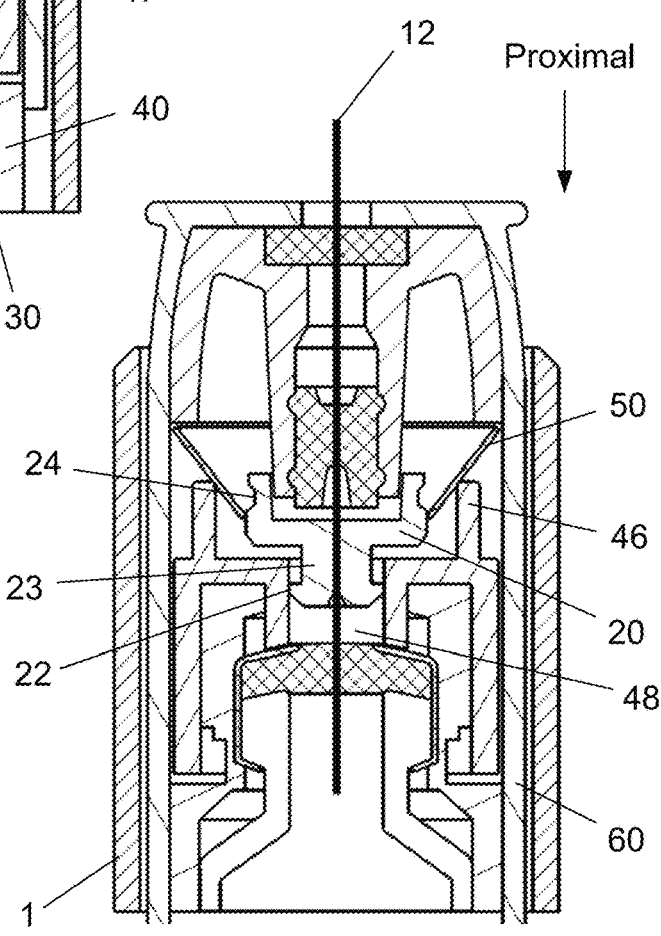
Fig. 3

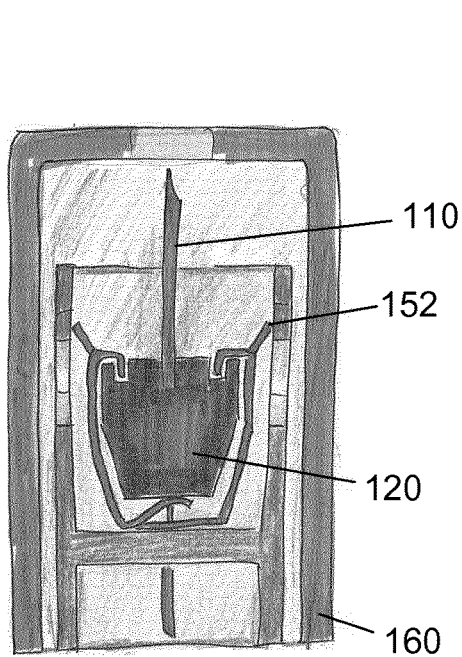
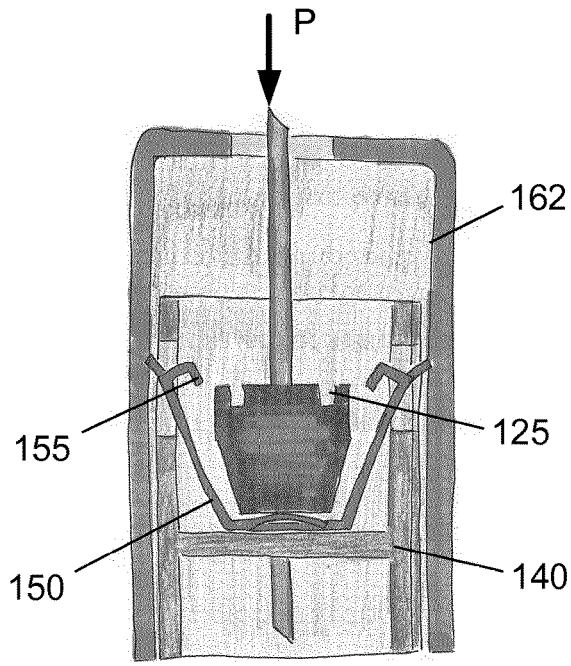
Fig. 5A    Fig. 5B
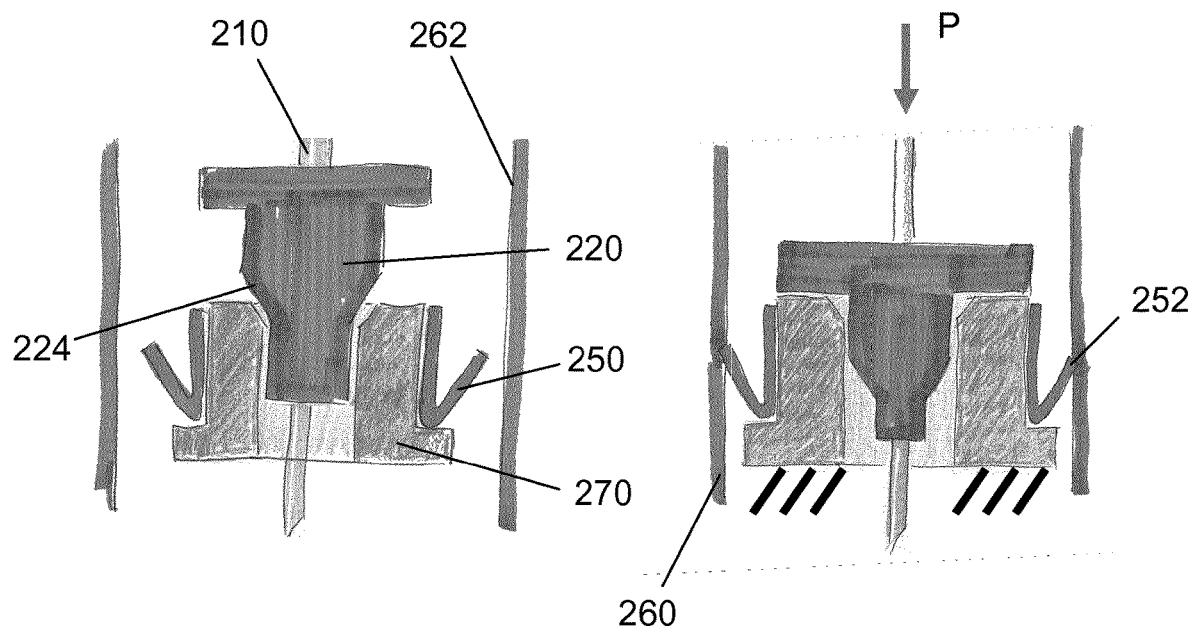
Fig. 6A    Fig. 6B

SHIELDED NEEDLE CANNULA

CROSS-REFERENCE TO RELATED APPLICATIONS

This application is a 35 U.S.C. § 371 National Stage application of International Application PCT/EP2016/077434 (published as WO 2017/084976), filed Nov. 11, 2016, which claims priority to European Patent Application 15195375.9, filed Nov. 19, 2015, the contents thereof which are incorporated by reference in their entirety.

THE TECHNICAL FIELD OF THE INVENTION

The invention relates to an injection system comprising an injection device carrying a shielded needle cannula. The invention alternatively relates to a shielded injection needle assembly attachable to an injection device to form an injection system. The invention especially relates to such injection system wherein the injection device is rendered unusable should the needle cannula be damaged.

DESCRIPTION OF RELATED ART

WO 01/91837 discloses a safety needle assembly in which a needle cannula is secured to a hub. A shield covering the needle cannula is guided on the outside of the hub and urged in the distal direction by a spring encompassed between the hub and the shield. The hub further carries means for attaching the safety needle assembly to an injection device.

Once the safety needle cannula is mounted onto an injection device, the injection system is ready for use. However, occasionally it happens that the user drops the combined injection device and safety needle assembly onto a hard surface such as a table or a floor. Should the distal end of the needle shield encounter such hard surface it sometimes happens that the distal tip of the needle cannula due to the impact is forced to be exposed and unfortunately also damaged. When the user here after picks up the injection device there is no visual signal indicating that the needle has been damaged. The consequence can either be that the injection to follow is rather painful or that the passage through the needle cannula is fully or partly blocked due to bending of the needle cannula.

DESCRIPTION OF THE INVENTION

It is an object of the present invention to provide a shielded needle cannula forming part of an injection system wherein the injection device of the system is automatically locked from further use should the distal tip of the needle cannula be exposed to an axial force above a predetermined level.

The invention is defined in claim 1 and followed by a number of more specific embodiments.

The invention can either be in the form of an injection system comprising an injection device and a shielded needle cannula connected to the injection device e.g. by a permanent connection. Alternatively the invention can be in the form of a needle assembly to be connected to an injection device.

Also in both alternatives, the needle shield covering the needle cannula can be provided with a cleaning reservoir for cleaning the distal tip of the needle cannula between injections such that the same needle cannula can be used for a multiple number of subsequent injections. As disclosed in WO 2015/062845 the cleaning reservoir is preferably filled with the same preservative containing liquid drug as contained in the injection device.

An injection system according to claim 1 comprises an injection device and a needle cannula. The needle cannula is mounted to a hub and preferably permanently connected to the injection device which is usually prefilled with a specific volume of liquid drug. The needle cannula is thus used for several injections and once the quantum of liquid drug in the embedded cartridge in the prefilled injection device is used the user discards the prefilled injection device together with the permanently attached needle cannula. However, although the needle cannula is permanently attached it can e.g. together with the hub be movable in relation to the remaining injection device, e.g. in an axial direction.

The distal tip of the needle cannula is covered by an axially movable needle shield which is movable between a first position and second position;

the first position being a position in which the distal tip of the needle cannula is covered by the axially movable needle shield, the second position being a position in which the distal tip of the needle cannula is exposed.

In order to irreversible lock the needle shield if the needle cannula is damaged a locking mechanism is provided. This locking mechanism locks the needle shield from axial movement in response to the needle cannula being exposed to an axial force above a predetermined value which axial force move the needle cannula and the hub in the proximal direction.

The impact or axial force is usually exposed onto the distal tip of the needle cannula which is usually the part first hitting the surface upon which the injection device is dropped.

Should the user thus drop the injection system such that the needle cannula is damaged, the injection device of the system would automatically be immobilized and further use thereof thus prevented.

In one aspect of the invention, the needle cannula is mounted, e.g. by gluing, in a hub which is axially movable. When the distal tip of the needle cannula encounters the surface upon which the injection device is dropped, both the needle cannula and the hub to which the needle cannula is mounted moves in the proximal direction which activates the locking mechanism.

The locking mechanism comprises in one example a locking element which is able to operate from a first state to a second state in response to the axial force exposed on the needle cannula i.e. when the force impacted on the distal tip of the needle cannula surpassed a certain predetermined level, the locking element automatically shifts to the second state.

In one example the hub is provided with an indentation into which the locking element is moved when the hub slides proximally upon impact.

In the first state, the locking element defines an outer diameter smaller than the inside diameter of the needle shield. The locking element is not necessarily circular and the outer diameter defined can be an imaginary outer diameter connecting outer points of the locking element.

In the second state the locking element is expanded in a radial direction to an outer diameter larger than the inside diameter of the needle shield. Once the locking element is expanded to engage the needle shield it prevents further axial movement of the needle shield which is thus locked. The injection system is thus immobilized and the injection device of the system is prevented from being used. As the locking element is not necessarily circular only a part of the outer diameter actually need to engage the inside diameter of the needle shield.

In one embodiment, the locking element is a metallic disc operable between the first state and the second state. The disc is preferably formed as a flat open ring-shaped element which can be bended in a direction perpendicular to its lateral extension. Once bended into the first state, the metallic disc is pre-tensed.

Upon activation, the metallic disc is released into the second state. The activation, or release, into the second state happens in response to an axial movement of the needle cannula and the hub.

In the case where the needle cannula is permanently connected to the injection device this is often done by connecting the needle cannula to a hub which hub is then embedded into the housing structure of the injection device. In such case axial movement of the needle cannula is transferred to axial movement of the hub as well.

In such example wherein the needle cannula is secured in a hub, the metallic disc has an inner opening sliding on an outer surface of the hub and the hub is axially movable relatively to the metallic dish which thus enters a track formed in the outer surface of the hub. Once the inner opening of the dish encounters the track, the diameter of the inner opening becomes even smaller due to the tension in the metallic disc. As the diameter of the inner opening decreases, the metallic disc flexes in the axial direction of the injection device and the axial height of the metallic disc becomes smaller and as a result the outer diameter expands and becomes larger.

This larger outer diameter engages with the inside surface of the needle shield and prevents further axial movement of the needle shield.

In another embodiment, the locking element is a metallic spring element operable between the first state and the second state and as in the first embodiment the releasing into the secand state is actuated is response to an axial movement of the needle cannula, and in case the needle cannula is secured in a hub also in response to axial movement of the hub.

As an alternative to an injection system, the invention can also be materialized in the form of a shielded injection needle assembly. Such shielded injection needle assembly comprises a needle cannula secured in a hub, and an axially movable needle shield movable between a first position and second position;
  the first position being a position in which the distal tip of
    the needle cannula is covered by the axially movable
    needle shield,
  the second position being a position in which the distal tip
    of the needle cannula is exposed.

Further a locking mechanism is provided for locking telescopically movement of the needle shield in response to the needle cannula being exposed to an axial force above a predetermined value which axial force move the needle cannula and the hub in the proximal direction.

The shielded injection needle assembly is preferably provided with means for attaching the needle assembly to an injection device to form a complete injection system and as in the first embodiment, the locking mechanism comprises a locking element which is able to operate from a first state to a second state in response to the axial force exposed on the needle cannula.

In the first state, the locking element defines an outer diameter smaller than the inside diameter of the needle shield and in the second state, the locking element is expanded in a radial direction to a diameter larger than the inside diameter of the needle shield thus locking the needle shield form further axial movement.

The described solutions of the first embodiment can easily be incorporated in the shielded injection needle embodiment.

Definitions

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854.

As used herein, the term "liquid drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The term "preservative containing liquid drug" is meant to encompass any liquid drug containing any amount of a preservative. The preservative used in liquid drugs are often meta-cresol or phenol but could in fact be any kind of preservative hindering or limiting the growth of bacteria.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible— can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

The term "Permanently connected" or "permanently embedded" as used in this description is intended to mean that the parts in question requires the use of tools in order to be separated and should the parts be separated it would permanently damage at least one of the parts thereby rendering the so disconnected parts inoperable.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention. The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which:

FIG. 1 show a cross-sectional view of the injection system when not in use.

FIG. 2 show a view of the locking element in a flat condition.

FIG. 3 show a cross-sectional view of the injection system during injection.

FIG. 5A-B show an example in which the locking element is a releasable spring element.

FIG. 6A-B show a different example with an alternative locking element.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Figure 4:
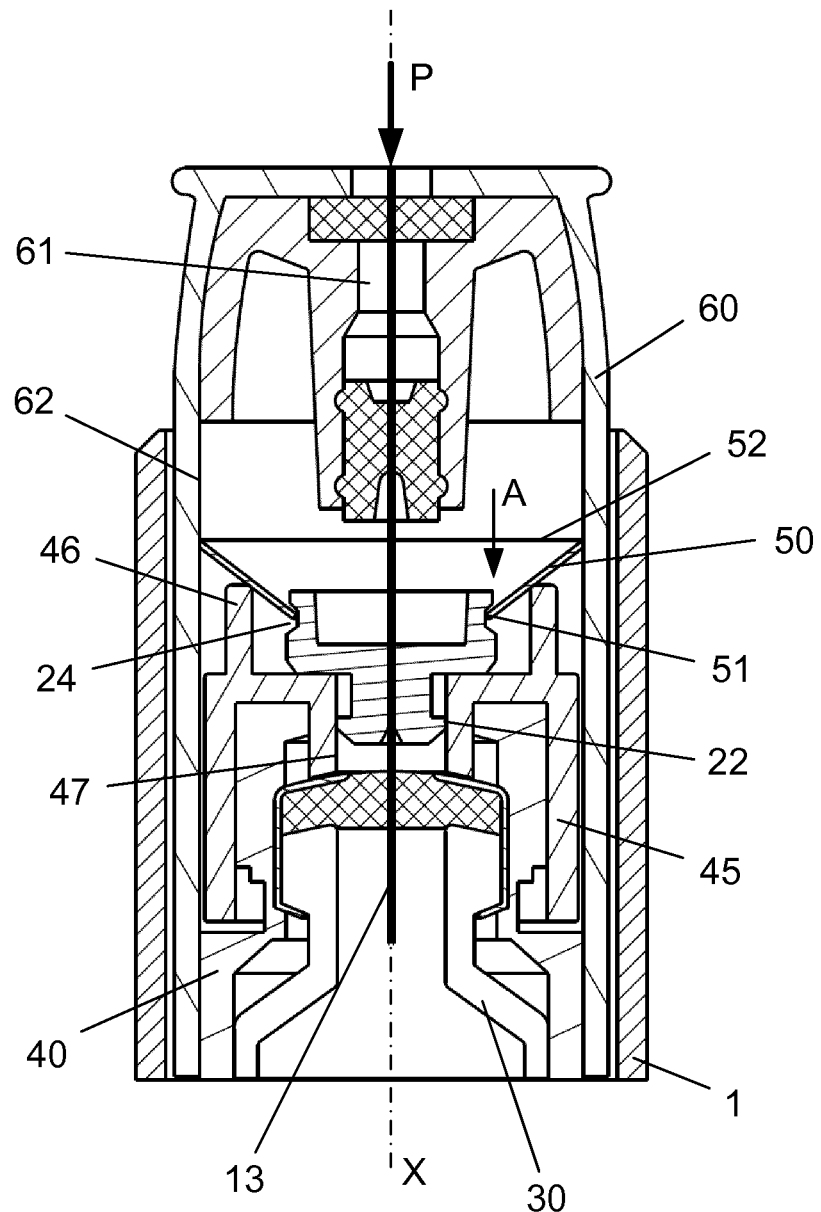
FIG. 4 show a cross-sectional view of the injection system with the locking mechanism activated.

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the needle cannula actually penetrating the skin of the user during injection whereas the term "proximal end" is meant to refer to the opposite end pointing away from the skin of the user during injection.

Distal and proximal are meant to be along an axial orientation extending along the longitudinal axis "X" of the injection device and is further indicated in the attached figures.

FIG. 1 discloses the injection system according to a first embodiment in which a needle cannula 10 is permanently secured to an injection device 1.

The needle cannula 10 is secured in a hub 20 which is axially movable in relation to a housing structure as will be explained. The needle cannula 10 comprises a distal part 11 with a distal tip 12 for penetrating the skin of a user, and a proximal part 13. In the depicted embodiment, the proximal part 13 is inserted into a cartridge 30 containing the liquid drug to be injected.

The cartridge 30 is distally provided with a septum 31 through which the proximal part 13 of the needle cannula 10 is inserted. The cartridge 30 is further secured in a housing assembly 40.

Such housing assembly 40 usually comprises a number of different parts. As can be seen in the FIGS. 1 to 3, the distal end of the cartridge 30 abuts a holding part 45 formed as a part of the housing assembly 40.

This holding part 45 is distally provided with a ring-shaped protrusion 46 which supports a locking element 50 which in this embodiment is formed as a metallic disc 50 operable between two different states.

An example of such metallic disc 50 is provided in FIG. 2 where it is disclosed in a flat condition i.e. before it is mounted in the injection system. The metallic disc 50 defines an inner opening 51 and an outer diameter 52. As can be seen from FIG. 2, the outer diameter 52 is formed by the outer ends of a plurality of fingers and is in FIG. 2 indicated by a broken line.

The metallic disc 50 can have a variety of different shapes. The important factor being that it is operable between a first state having one outer diameter and a second state having a larger outer diameter. In the example given the metallic disc 50 is formed in a pattern which can be bended in a direction transverse to FIG. 2 whereby tension is introduced in the metallic disc 50. Once the metallic disc 50 is bended in the transverse direction a change of the diameter of the inner opening 51 will result in a similar change of the outer diameter 52.

In the first state as disclosed in FIGS. 1 and 2, the inner opening 51 of the metallic disc 50 is fitted around the outside surface 21 of the hub 20 which thus forces the outer diameter 52 inwardly.

The hub 20 which secures the needle cannula 10 slides in on an internal surface 47 of a tubular opening 48 provided in the holding part 45.

In the initial position, prior to performing an injection, the distal tip 12 of the needle cannula 10 is concealed behind a axially movable needle shield 60.

This needle shield 60 is urged in the distal direction by not shown spring means and further carries a cleaning chamber 61 containing a cleaning agent for cleaning the distal tip 12 of the needle cannula 10 between subsequent injections such that the same needle cannula 10 can be used for multiple injections.

If now a user drops the injection device 1 on to a hard surface such as a table or a floor, there is a possibility that the distal tip 12 of the needle cannula 10 could be damaged.

As can be seen from FIGS. 1, 3 and 4, the hub 20 is movable mounted in the tubular opening 48 of the holding part 45 such that if the distal tip 12 of the needle cannula 10 is exposed to a force larger than the holding force between the inside surface 47 of the tubular opening 48 and the outer surface 22 of the hub 20, the hub 20 will be forced to move axially in the proximal direction as indicated by the arrow "A" in FIG. 4.

As can be seen from the FIGS. 1 to 3, the outer surface 22 of the hub 20 is provided on a proximal extension 23 which extend into the tubular opening 48 of the holding part 45.

The metallic disc 50 is mounted on the outside surface 21 of the hub 20. However this outside surface 21 is provided with a circular track 24 into which the inner opening 51 of the metallic disc 50 will move when the hub 20 slides axially in the proximal direction. This position is disclosed in FIG. 3. Due to the inherent tension in the metallic disc 50 it will shift to the second state and the outer diameter 52 will expand in a radial direction.

The inside surface of the needle shield 60 has an inside diameter 62 which allows the needle shield 60 to slide axially when the metallic disc 50 is in the first position. In this state, the outer diameter 52 of the metallic disc 50 is smaller than the inside diameter 62 of the needle shield 60.

When the hub 20 and the metallic disc 50 is slided relative to each other and the inner opening 51 of the metallic disc 50 is located in the track 24, the outer diameter 52 of the metallic disc 50 has expanded radially such that the outer diameter 52 of the metallic disc 50 now is larger than the inside diameter 62 of the needle shield 60.

The needle shield 60 is therefore locked and hindered in axial movement when the metallic disc 50 is in the second state which thus renders the injection device 1 unusable.

FIG. 5A-B discloses a different embodiment in which a spring element 150 is releasable secured to the hub 120. Once the needle cannula 110 is exposed to a force "P" surpassing a predetermined value, the needle cannula 110 and the hub 120 is pushed axially in the proximal direction which releases the spring element 150 to expand to an outer diameter 152 being larger than the inside diameter 162 of the needle shield 160.

In the first state, the metallic spring element 150 has a number of hooks 155 which engages similar recesses 125 provided in the hub 120. When the hub 120 is moved proximally these hooks 155 are released and the inherent tension in the metallic spring element 150 forces the outer diameter 152 of the metallic spring element 150 to expand radially and engage with the inside diameter 162 of the needle shield 160.

The radial expansion of the metallic spring element 150 could e.g. be done through an opening in the housing assembly 140 as depicted in FIG. 5A-B.

A further embodiment is disclosed in FIG. 6A-B. In this embodiment a metallic element 250 is forced to move radially when the hub 220 moves axially in the proximal direction. The hub 220 is provided with a conical area 224 which forces an intermediate element 270 carrying the metallic element 250 to expand radially.

The radial expansion of the intermediate element 270 also forces the metallic element 250 to move radially and engage with the inside diameter 262 of the needle shield 260 thus rendering the injection device unusable.

Some preferred embodiments have been shown in the foregoing, but it should be stressed that the invention is not limited to these, but may be embodied in other ways within the subject matter defined in the following claims.

The invention claimed is:
1. An injection system comprising;
an injection device,
a needle cannula having a distal part with a distal tip and a proximal part,
wherein the needle cannula is mounted in a hub and further permanently secured to the injection device, and
an axially movable needle shield movable between a first position and second position;
the first position being a position in which the distal tip of the needle cannula is covered by the axially movable needle shield,
the second position being a position in which the distal tip of the needle cannula is exposed, wherein
a locking mechanism comprising a locking element is provided for irreversibly locking telescopic movement of the axially movable needle shield, the locking element or locking mechanism locks the needle shield from axial movement in response to the needle cannula being exposed to an axial force (P) above a predetermined value which axial force move the needle cannula and the hub in the proximal direction, and
wherein, in response to the axial force (P) exposed on the needle cannula, the locking element operates from a first state to a second state and the hub moves relatively to the locking element.

2. The injection system according to claim 1, wherein the locking element in the first state defines an outer diameter smaller than the inside diameter of the needle shield.

3. The injection system according to claim 2, wherein the locking element in the second state is expanded in a radial direction to an outer diameter larger than the inside diameter of the needle shield.

4. The injection system according to claim 1, wherein the locking element is a metallic disc operable between the first state and the second state.

5. The injection system according to claim 4, wherein the metallic disc is pre-tensed in the first state and released into the second state in response to the axial movement of the hub.

6. The injection system according to claim 5, wherein the metallic disc has an inner opening sliding on an outer surface of a hub securing the needle cannula and which hub is axially movable relatively to metallic dish such that the metallic disc enter a track formed in the outer surface of the hub.

7. The injection system according to claim 1, wherein the locking element is a metallic spring element operable between the first state and the second state.

8. The injection system according to claim 7, wherein the releasing into the second state is actuated is response to an axial movement of the needle cannula and the hub.

9. A shielded injection needle assembly, comprising;
a needle cannula having a distal part with a distal tip and a proximal part, which needle cannula is secured in a hub, and
a axially movable needle shield movable between a first position and second position;
the first position being a position in which the distal tip of the needle cannula is covered by the axially movable needle shield,
the second position being a position in which the distal tip of the needle cannula is exposed, wherein
a locking mechanism is provided for locking telescopically movement of the needle shield in response to the needle cannula being exposed to an axial force (P) above a predetermined value which axial force move the needle cannula and the hub in the proximal direction,
wherein the locking mechanism comprises a locking element which is able to operate from a first state to a second state in response to the axial force exposed on the needle cannula, and
wherein the hub moves relatively to the locking element.

10. The injection system according to claim 9, wherein the hub is provided with an indentation.

11. The shielded injection needle assembly according to claim 9, wherein the locking element in the first state defines an outer diameter smaller than the inside diameter of the needle shield.

12. The shielded injection needle assembly according to claim 1, wherein the locking element in the second state is expanded in a radial direction to a diameter larger than the inside diameter of the needle shield.

* * * * *

UNITED STATES PATENT AND TRADEMARK OFFICE
CERTIFICATE OF CORRECTION

PATENT NO. : 10,828,427 B2
APPLICATION NO. : 15/773399
DATED : November 10, 2020
INVENTOR(S) : Larsen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 127 days.

Signed and Sealed this
Fourteenth Day of February, 2023

Katherine Kelly Vidal
*Director of the United States Patent and Trademark Office*